US012690835B2

(12) United States Patent
Zhu

(10) Patent No.: US 12,690,835 B2
(45) Date of Patent: Jul. 28, 2026

(54) METHOD FOR ULTRASONICALLY MEASURING HEART RATE VIA FINGER, APPARATUS FOR ULTRASONICALLY MEASURING HEART RATE VIA FINGER, ELECTRONIC DEVICE, AND STORAGE MEDIUM

(71) Applicant: HUIKE (SINGAPORE) HOLDING PTE. LTD., Singapore (SG)

(72) Inventor: Jun Zhu, Shenzhen (CN)

(73) Assignee: HUIKE (SINGAPORE) HOLDING PTE. LTD., Singapore (SG)

( * ) Notice: Subject to any disclaimer, the term of this patent is extended or adjusted under 35 U.S.C. 154(b) by 0 days.

(21) Appl. No.: 18/989,653

(22) Filed: Dec. 20, 2024

(65) Prior Publication Data

US 2025/0114062 A1 Apr. 10, 2025

Related U.S. Application Data

(63) Continuation of application No. PCT/CN2024/107337, filed on Jul. 24, 2024.

(30) Foreign Application Priority Data

Sep. 27, 2023 (CN) .......................... 202311286849.5

(51) Int. Cl.
*A61B 8/02* (2006.01)
*A61B 8/00* (2006.01)
(52) U.S. Cl.
CPC .............. *A61B 8/02* (2013.01); *A61B 8/5207* (2013.01)
(58) Field of Classification Search
CPC ........ A61B 8/02; A61B 8/5207; A61B 8/5223
See application file for complete search history.

(56) References Cited

U.S. PATENT DOCUMENTS

2016/0313439 A1* 10/2016 Min ................... G06V 40/1306
2019/0370518 A1* 12/2019 Maor ........................ A61B 8/02
(Continued)

FOREIGN PATENT DOCUMENTS

CN 110742653 A 2/2020
CN 113993460 A 1/2022
(Continued)

OTHER PUBLICATIONS

A. Shahshahani, D. R. Nafchi and Z. Zilic, "Ultrasound sensors and its application in human heart rate monitoring," 2017 IEEE International Symposium on Circuits and Systems (ISCAS), Baltimore, MD, USA, 2017, pp. 1-4, doi: 10.1109/ISCAS.2017.8050899. (Year: 2017).*
(Continued)

*Primary Examiner* — Chao Sheng
(74) *Attorney, Agent, or Firm* — Emerson, Thomson & Bennett, LLC; Roger D. Emerson; Peter R. Detorre

(57) ABSTRACT

A method and apparatus for ultrasonically measuring a heart rate via a finger, and an electronic device are provided. The method includes: acquiring, when the finger presses the screen, a correspondence function between an echo signal and a fly time, and determining a target fly time based on the correspondence function, wherein the fly time is time elapsed from transmission to reception of an ultrasonic signal; transmitting the ultrasonic signal to the finger, receiving a current echo frame returned from the finger and carrying fingerprint information of the finger based on the target fly time; determining a time domain sampling signal based on an inter-frame difference between the current echo frame and a reference frame; and calculating a heart rate value based on the time domain sampling signal. Through the above steps, heart rate measurement can be achieved through a finger based on an ultrasonic fingerprint apparatus.

12 Claims, 7 Drawing Sheets

(56) References Cited

U.S. PATENT DOCUMENTS

2020/0184176 A1    6/2020  Liu et al.
2021/0100523 A1*  4/2021  Jiang ...................... A61B 8/488
2022/0019313 A1*  1/2022  He .......................... G01F 1/662

FOREIGN PATENT DOCUMENTS

CN        116616817 A  *  8/2023  .............. A61B 8/02
CN        117338332 A     1/2024

OTHER PUBLICATIONS

International Search Report of PCT/CN2024/107337 issued by CNIPA on Oct. 23, 2024.
Shahshahani, Amirhossein et al. "Ultrasound sensors and its application in human heart rate monitoring." 2017 IEEE International Symposium on Circuits and Systems (ISCAS), May 31, 2017, p. 1-4.

* cited by examiner

Start — S51

Collecting a current echo frame — S52

Updating a reference frame — S53

Time domain sampling point=Mean(Abs(Signal-Base)>TH4) — S54

S2401

Filtering the time domain sampling signal to obtain a filtered time domain sampling signal

S2402

Calculating the heart rate value based on the filtered time domain sampling signal

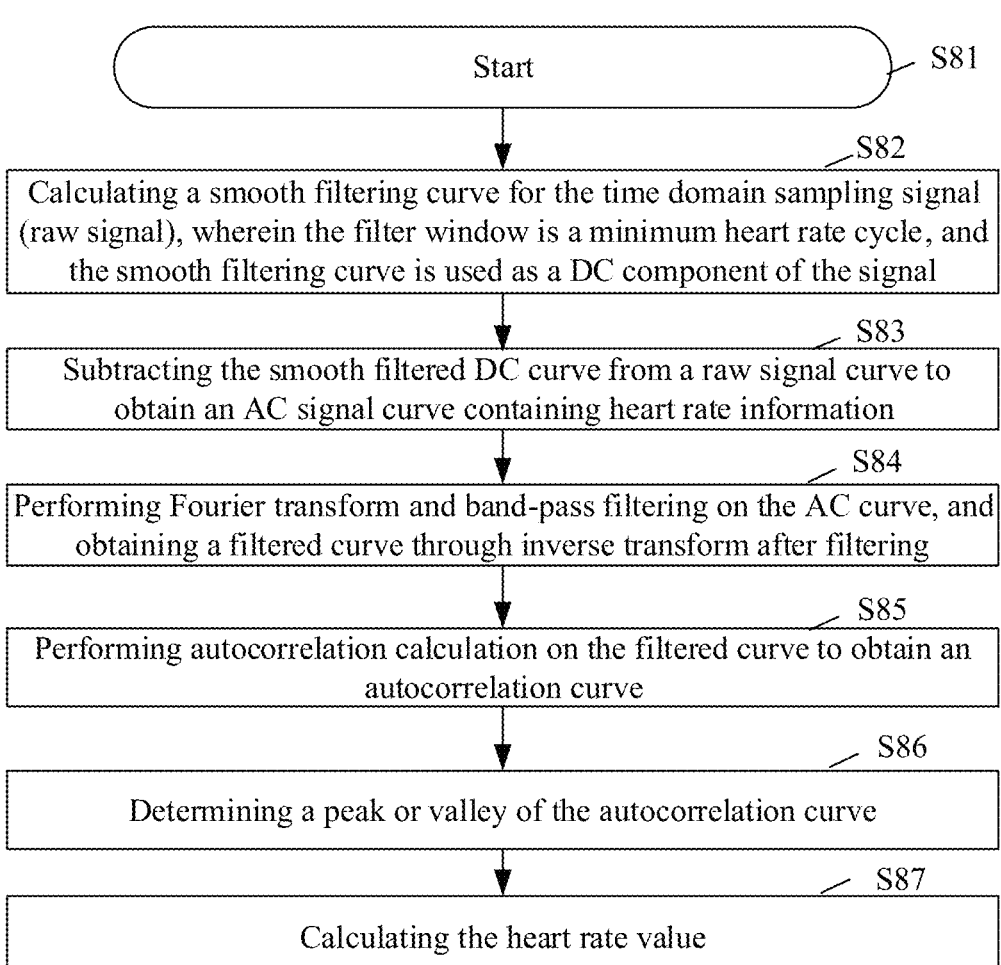

Start ⟶ S81

Calculating a smooth filtering curve for the time domain sampling signal (raw signal), wherein the filter window is a minimum heart rate cycle, and the smooth filtering curve is used as a DC component of the signal ⟶ S82

Subtracting the smooth filtered DC curve from a raw signal curve to obtain an AC signal curve containing heart rate information ⟶ S83

Performing Fourier transform and band-pass filtering on the AC curve, and obtaining a filtered curve through inverse transform after filtering ⟶ S84

Performing autocorrelation calculation on the filtered curve to obtain an autocorrelation curve ⟶ S85

Determining a peak or valley of the autocorrelation curve ⟶ S86

Calculating the heart rate value ⟶ S87

FIG. 8

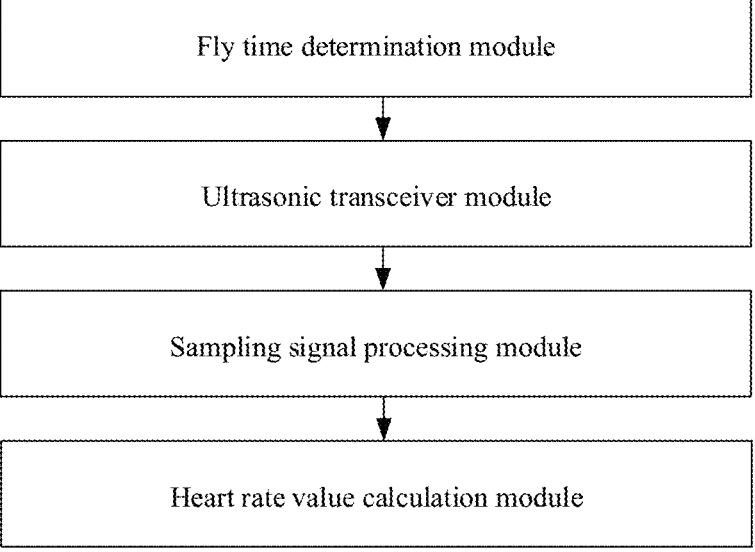

Fly time determination module

Ultrasonic transceiver module

Sampling signal processing module

Heart rate value calculation module

FIG. 9

METHOD FOR ULTRASONICALLY MEASURING HEART RATE VIA FINGER, APPARATUS FOR ULTRASONICALLY MEASURING HEART RATE VIA FINGER, ELECTRONIC DEVICE, AND STORAGE MEDIUM

CROSS REFERENCE TO RELATED APPLICATIONS

The present disclosure is a continuation of International Application No. PCT/CN2024/107337, filed on Jul. 24, 2024, which claims priority to Chinese Patent Application No. "202311286849.5" titled "METHOD FOR ULTRA-SONICALLY MEASURING HEART RATE VIA FINGER, APPARATUS FOR ULTRASONICALLY MEASURING HEART RATE VIA FINGER, ELECTRONIC DEVICE, AND STORAGE MEDIUM" and filed on 27 Sep. 2023, both of which are incorporated herein by reference in their entireties.

TECHNICAL FIELD

Embodiments of the present disclosure relate to the technical field of ultrasonic signal processing, and particularly relate to a method for ultrasonically measuring a heart rate via a finger, an apparatus for ultrasonically measuring a heart rate via a finger, an electronic device, and a storage medium.

BACKGROUND

With the rapid development of the electronic device industry, there is an increasing demand for biometric identification technologies in various fields. Fingerprint identification is one of the most important identification methods. Mature fingerprint collection solutions include optical fingerprint collection and capacitive fingerprint collection. In recent years, ultrasonic fingerprint technology has become a novel fingerprint development direction.

In an optical fingerprint chip, heart rates can be measured by photoplethysmography. However, an ultrasonic fingerprint chip uses acoustic wave technology and fails to measure a heart rate signal using optical principles. A new method is required to measure a human heart rate signal while ultrasonic fingerprint identification is performed.

SUMMARY

In view of this, embodiments of the present disclosure provide a method for ultrasonically measuring a heart rate via a finger, an apparatus for ultrasonically measuring a heart rate via a finger, an electronic device, and a storage medium, to at least partially solve the above problems.

According to an embodiment in a first aspect of the present disclosure, a method for ultrasonically measuring a heart rate via a finger is provided, being applied to an ultrasonic fingerprint apparatus, the ultrasonic fingerprint apparatus being arranged below a cover sheet of an electronic device to implement under-display ultrasonic fingerprint identification, the method comprising: acquiring, when the finger presses a screen, a correspondence function between an echo signal and a fly time, and determining a target fly time based on the correspondence function, wherein the fly time is a time elapsed from transmission to reception of an ultrasonic signal; transmitting the ultrasonic signal to the finger, and receiving a current echo frame that is returned from the finger and carries fingerprint information of the finger based on the target fly time; determining a time domain sampling signal based on an inter-frame difference between the current echo frame and a reference frame; and calculating a heart rate value based on the time domain sampling signal.

In another implementation of the present disclosure, the determining the target fly time based on the correspondence function comprises: determining a peak value of the correspondence function based on the correspondence function; and determining the target fly time based on the peak value of the correspondence function, wherein the target fly time is a fly time corresponding the obtaining of a maximum echo signal.

In another implementation of the present disclosure, the method further comprises: calculating an inter-frame difference between the current echo frame and a last echo frame; and using, in response to the difference satisfying an inter-frame difference threshold, the current echo frame as the reference frame.

In another implementation of the present disclosure, the using, in response to the difference satisfying the inter-frame difference threshold, the current echo frame as the reference frame comprises: calculating a continuous count value of current echo frames that satisfy the inter-frame difference threshold; and using, in response to the continuous count value satisfying a count threshold, any one of the current echo frames that satisfy the inter-frame difference threshold and correspond to the continuous count value as the reference frame.

In another implementation of the present disclosure, the determining the time domain sampling signal based on the inter-frame difference between the current echo frame and the reference frame comprises: calculating a reference difference between the current echo frame and the reference frame, using the reference difference as time domain sampling data of the current echo frame; and determining the time domain sampling signal based on the time domain sampling data.

In another implementation of the present disclosure, the using the reference difference as the time domain sampling data of the current echo frame comprises: using, in response to the reference difference satisfying a reference difference threshold, the reference difference as the time domain sampling data of the current echo frame.

In another implementation of the present disclosure, the calculating the heart rate value based on the time domain sampling signal comprises: filtering the time domain sampling signal to obtain a filtered time domain sampling signal; and calculating the heart rate value based on the filtered time domain sampling signal.

According to an embodiment in a second aspect of the present disclosure, an apparatus for ultrasonically measuring a heart rate via a finger is provided, comprising: a fly time determination module configured to acquire, when the finger presses a screen, a correspondence function between an echo signal and a fly time, and determine a target fly time based on the correspondence function, wherein the fly time is a time elapsed from transmission to reception of an ultrasonic signal; an ultrasonic transceiver module configured to transmit the ultrasonic signal to the finger, and receive a current echo frame that is returned from the finger and carries fingerprint information of the finger based on the target fly time; a sampling signal processing module configured to determine a time domain sampling signal based on an inter-frame difference between the current echo frame and a reference frame; and a heart rate value calculation module configured to calculate a heart rate value based on the time domain sampling signal.

According to an embodiment in a third aspect of the present disclosure, an electronic device is provided, including: a processor, a memory, a communication interface, and a communication bus, wherein the processor, the memory, and the communication interface communicate with each other through the communication bus; and the memory is configured to store at least one executable instruction, wherein the executable instruction is executed to cause the processor to execute operations corresponding to the method as described in the first aspect.

According to an embodiment in a fourth aspect of the present disclosure, a computer storage medium is provided, storing a computer program thereon, wherein the program, when executed by a processor, implements the method as described in the first aspect.

In the solutions of the embodiments of the present disclosure, based on the ultrasonic echo signal obtained when the finger presses the screen, a human heart rate can be measured during fingerprint identification, thereby additionally providing the ultrasonic fingerprint apparatus with a heart rate detection function without increasing the hardware costs, and synchronously additionally providing various portable electronic devices using the ultrasonic fingerprint apparatus with the heart rate detection function.

BRIEF DESCRIPTION OF DRAWINGS

To more clearly describe technical solutions in embodiments of the present disclosure or the prior art, drawings to be used in the description of the embodiments or the prior art will be briefly introduced below. Apparently, the drawings in the description below are merely some embodiments disclosed in the embodiments of the present disclosure. For those of ordinary skills in the art, other drawings may also be obtained based on these drawings.

FIG. 8 is a flowchart of steps for calculating a heart rate according to an embodiment of the present disclosure.

FIG. 9 is a schematic diagram of a functional structure of an apparatus for ultrasonically measuring a heart rate via a finger according to an embodiment of the present disclosure.

DETAILED DESCRIPTION

Figure 1:
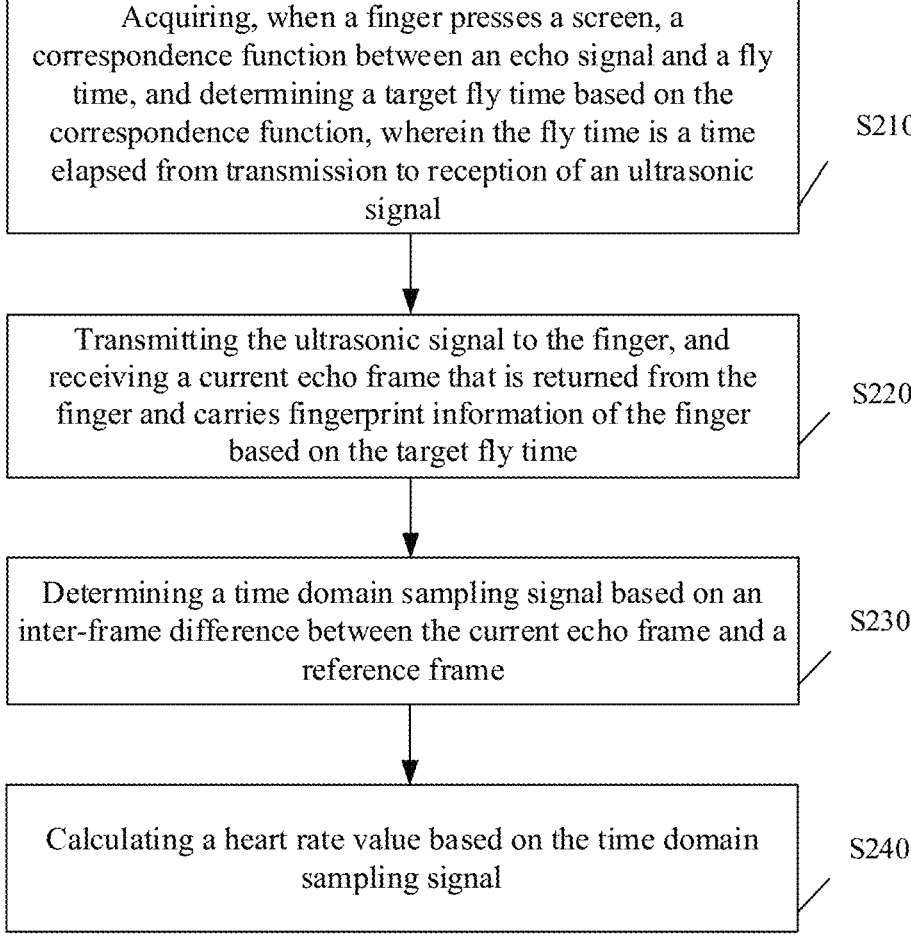
FIG. 1 is a flowchart of steps of a method for ultrasonically measuring a heart rate via a finger according to an embodiment of the present disclosure.

To enable those skilled in the art to better understand technical solutions of embodiments of the present disclosure, the technical solutions of the embodiments of the present disclosure will be clearly described in detail below with reference to drawings in the embodiments of the present disclosure. Apparently, the described embodiments are merely some, instead of all, of the embodiments of the present disclosure. All other embodiments obtained by those of ordinary skills in the art based on some embodiments among the embodiments of the present disclosure shall be encompassed within the scope of protection of the embodiments of the present disclosure.

It should be understood that the terms, such as "first," "second," and "third," in the claims, specification, and drawings of the present disclosure are used to distinguish between different objects, and are not used to describe a particular sequence. The terms "comprise" and "include" used in the specification and claims of the present disclosure indicate the presence of described features, integers, steps, operations, elements and/or components, but do not exclude the presence or addition of one or more other features, integers, steps, operations, elements, components and/or collections thereof.

It should be further understood that the terms used in the specification of the present disclosure are intended merely to describe particular embodiments, and are not intended to limit the present disclosure. As used in the specification and claims of the present disclosure, the singular forms "a," "an" and "the" are intended to include plural forms, unless the context clearly indicates otherwise. It should be further understood that the term "and/or" as used in the specification and claims of the present disclosure refers to any combination and all possible combinations of one or more of the associated listed items, and includes such combinations.

The structure of a human finger is mainly composed of phalanges, tendons, muscles, nerves, blood vessels, etc. Vasoconstriction and vasodilation of the finger will occur regularly with the heart rate, which will cause regular changes of the tissues, such as blood vessels and muscles. In the present disclosure, an ultrasonic wave is emitted into the inside of the finger, a signal reflected from the finger is received, the reflected signal image is analyzed, regular tissue changes thereof are extracted, and then the heart rate is calculated.

Description of the implementation principle: Due to different reflectivities of various parts of the finger structure to the acoustic wave signal, the phalanges have strongest signals to the acoustic wave. In order to collect better finger tissue echoes, an ultrasonic fly time needs to be adjusted to a value near the phalanges, so that a strongest ultrasonic echo is collected.

The ultrasonic fingerprint apparatus may be an ultrasonic chip, that is, a pixel point array with a resolution of M*N. Each pixel point can independently emit and receive an ultrasonic wave. When the chip is working, each pixel point starts to generate an ultrasonic wave through an ultrasonic transducer. After the generation is completed, and after the time of transmission of an acoustic wave defined as an fly time, the ultrasonic transducer at the pixel point begins to receive an ultrasonic echo, and converts the acoustic wave signal into an electrical signal. An M*N image collected by the ultrasonic chip is an acoustic echo image, which may also be referred to as an echo frame.

The finger tissues will dilate regularly with the heart beating, and changes of the muscle tissues will cause the transmission medium to change regularly after an ultrasonic signal is transmitted to the finger. This further affects the phase of the acoustic echo. The ultrasonic chip maintains a frame rate of n and integration time of t. Integration is performed on the finger at a constant frame rate based on a same fly time. Echoes after the phase change will be collected as a frame of image, that is, the echo frame. Continuous frame images of the ultrasonic echo signal are analyzed, and regular echo change signals between the continuous frame images are calculated, so that the heart rate in the finger can be extracted.

FIG. 1 shows an example process of a method for ultrasonically measuring a heart rate via a finger according to an embodiment of the present disclosure. The method for ultrasonically measuring a heart rate via a finger in this embodiment is applied to an ultrasonic fingerprint apparatus, wherein the ultrasonic fingerprint apparatus is arranged below a cover sheet of an electronic device to implement under-display ultrasonic fingerprint identification. The method includes:

S210: acquiring, when the finger presses the screen, a correspondence function between an echo signal and a fly time, and determining a target fly time based on the correspondence function, wherein the fly time is a time elapsed from transmission to reception of an ultrasonic signal.

Figure 2:
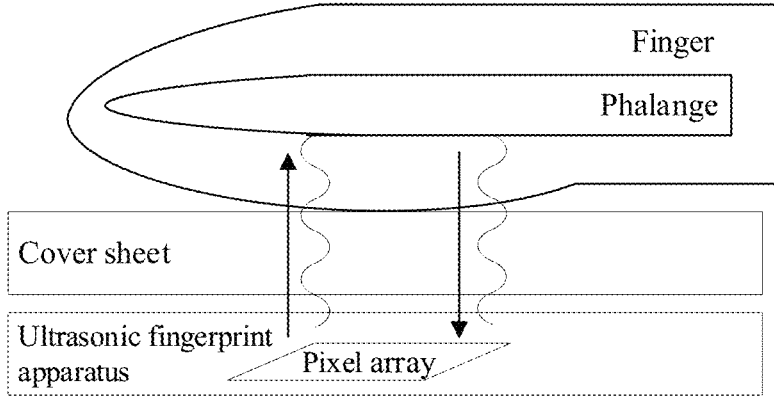
FIG. 2 is a schematic principle diagram of fingerprinting by an electronic device with an ultrasonic fingerprint apparatus according to an embodiment of the present disclosure.

It should be noted that, as shown in FIG. 2, the heart rate needs to be ultrasonically measured by transmitting the ultrasonic signal to the phalanges of the finger to obtain a larger echo signal. For example, an ultrasonic wave generated from an ultrasonic transducer penetrates the cover sheet, then enters the finger, and reaches the phalanges, so that a strong echo signal is reflected back to the ultrasonic transducer. In order to adapt to different fingers, it is necessary to determine an appropriate fly time, that is, the target fly time, by measurement after the finger presses, so that the measured echo signal is a strongest echo signal in the vicinity of the phalanges.

Figure 3:
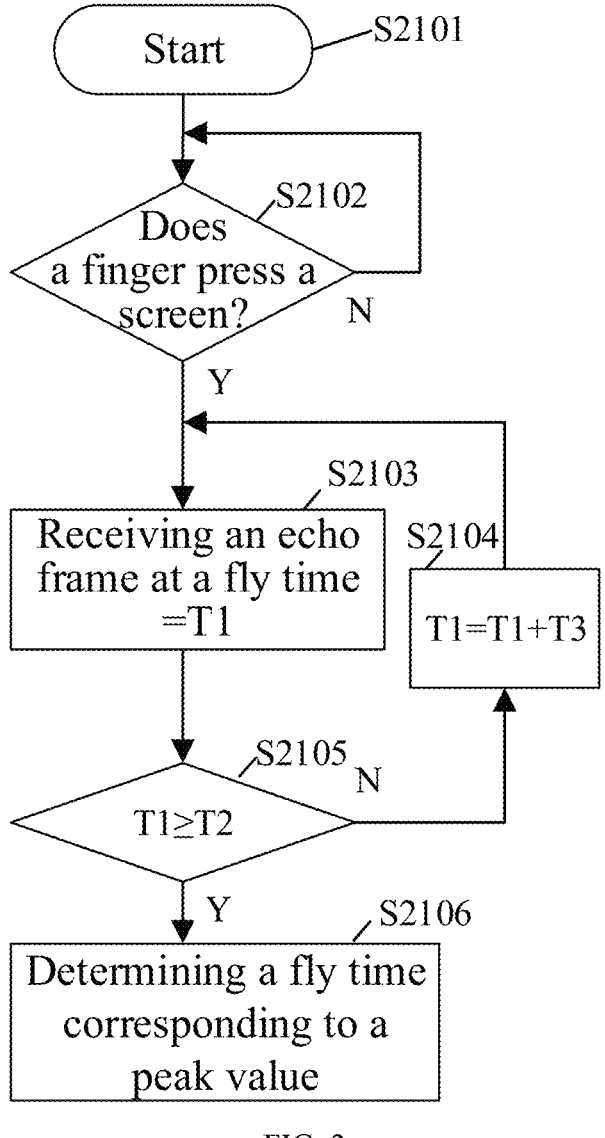
FIG. 3 is a flowchart of steps for determining a target fly time according to an embodiment of the present disclosure.

A process of determining the target fly time is as shown in FIG. 3. The process starts (S2101); determining whether the finger presses the screen (S2102); when the finger presses the screen, collecting, by an ultrasonic fingerprint apparatus an echo frame of a frame of image with a fly time T1 as the starting point (S2103); continuing image acquisition with the step time of T3 (S2104); determining whether the fly time is still within an interval T1-T2 (S2105); and selecting the fly time corresponding to a peak value of the echo signal in the interval T1-T2 as the target fly time used when the heart rate is measured via a current finger (S2106). The interval T1-T2 may be a manually determined empirical value.

S220: transmitting the ultrasonic signal to the finger, and receiving a current echo frame that is returned from the finger and carries fingerprint information of the finger based on the target fly time.

S230: determining a time domain sampling signal based on an inter-frame difference between the current echo frame and a reference frame.

S240: calculating a heart rate value based on the time domain sampling signal.

In the solutions of the embodiments of the present disclosure, based on the ultrasonic echo signal obtained when the finger presses the screen, a human heart rate can be measured during fingerprint identification, thereby additionally providing the ultrasonic fingerprint apparatus with a heart rate detection function without increasing the hardware costs, and synchronously additionally providing various portable electronic devices using the ultrasonic fingerprint apparatus with the heart rate detection function.

In a possible implementation, the determining the target fly time based on the correspondence function comprises: determining a peak value of the correspondence function based on the correspondence function; and determining the target fly time based on the peak value of the correspondence function, wherein the target fly time is a fly time corresponding to the obtaining of a maximum echo signal.

In a possible implementation, the method further includes: calculating a inter-frame difference between the current echo frame and a last echo frame; and using, in response to the difference satisfying an inter-frame difference threshold, the current echo frame as the reference frame.

In another implementation, the using, in response to the difference satisfying the inter-frame difference threshold, the current echo frame as the reference frame comprises: calculating a continuous count value of current echo frames that satisfy the inter-frame difference threshold; and using, in response to the continuous count value satisfying a count threshold, any one of the current echo frames that satisfy the inter-frame difference threshold and correspond to the continuous count value as the reference frame.

It should be noted that in order to extract regular heart rate signals between echo frames, a stable echo frame needs to be selected as the reference frame. Finger tissues change the fastest at a moment of systole, the finger tissues tend to be stable during diastole, and a frame when the finger tissues are stable is used as the reference frame.

A difference between each corresponding pixel point of the current echo frame and the last echo frame is calculated to ascertain the difference between the two frames of images, the image difference is quantified, a time point of the current echo frame with the continuous count value satisfying the count threshold TH3 is selected as a time point of diastole, and an average image of images of the current echo frame with the count value satisfying the count threshold TH3 is used as the reference frame. The time domain sampling signal will be calculated from all images collected after the reference frame is determined based on this reference frame. Since images are continuously collected, every frame of image, when collected, will be determined whether to satisfy a reference frame condition. If the reference frame condition is satisfied, the reference frame needs to be re-determined.

Figure 4:
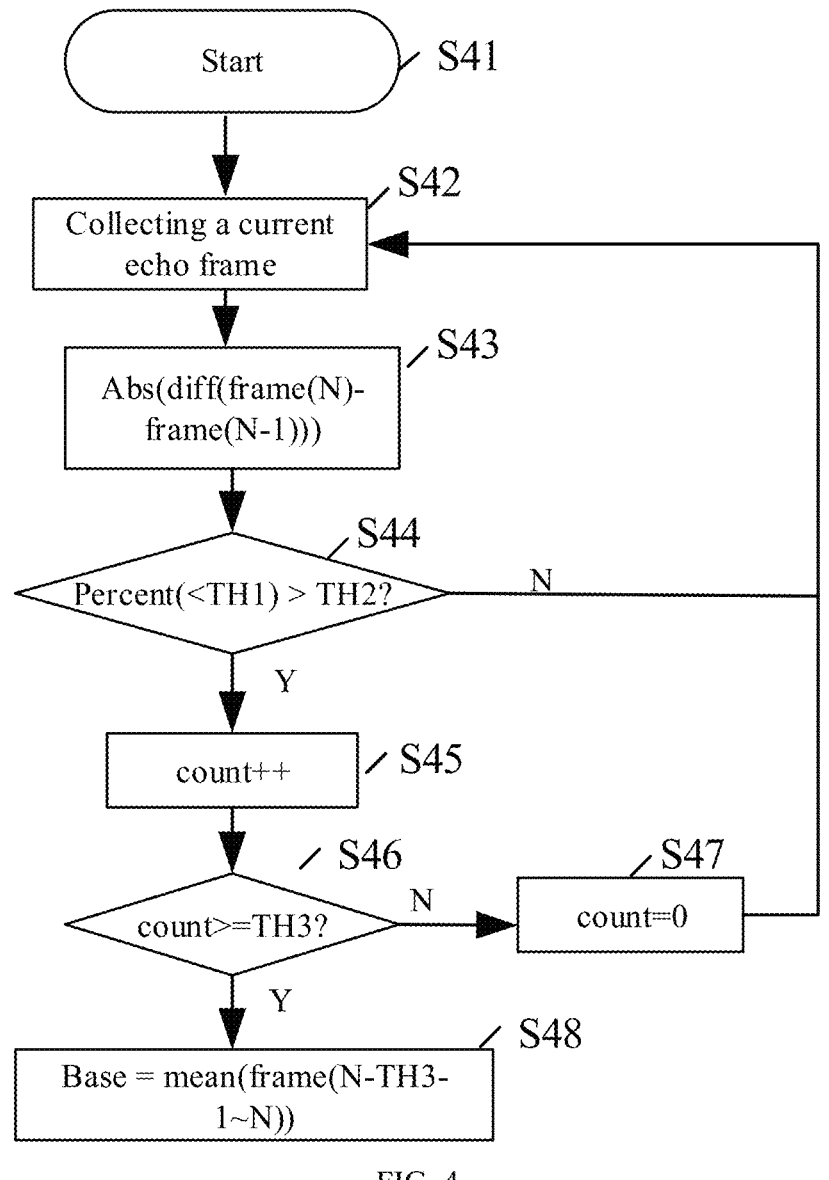
FIG. 4 is a flowchart of steps for determining a reference frame according to an embodiment of the present disclosure.

Specifically, a process of obtaining the reference frame is as shown in FIG. 4. The process starts (S41); collecting the current echo frame (S42); calculating a difference between pixel points corresponding to images of the current echo frame and the last echo frame, and using an absolute value of the difference as the inter-frame difference (S43); determining whether a percent of the inter-frame difference less than the inter-frame difference threshold TH1 is less than a percent threshold TH2 (S44); returning to the step S42, in response to failing to satisfy a reference frame determination condition when the percent is less than the percent threshold TH2, to continue collecting a next echo frame; calculating, in response to the percent being greater than or equal to the percent threshold TH2, the continuous count value of the current echo frame satisfying the inter-frame difference threshold (S46); determining whether the continuous count value is greater than or equal to the count threshold TH3 (S46); setting the count value to zero, in response to the continuous count value being less than the count threshold TH3, (S47), and returning to the step S42; and using, in response to the continuous count value being greater than or equal to the count threshold TH3, any current echo frame corresponding to the continuous count value and satisfying the inter-frame difference threshold as the reference frame (Base) (S48).

In another possible implementation, the determining the time domain sampling signal based on the inter-frame difference between the current echo frame and the reference frame comprises: calculating a reference difference between the current echo frame and the reference frame, using the reference difference as time domain sampling data of the current echo frame; and determining the time domain sampling signal based on the time domain sampling data.

It should be noted that the steps S220 and S230 may be processed concurrently. The echo frames in the step S220 will be continuously received at fixed intervals, and the determination of the time domain sampling signal in the step S230 may be executed once every 1 s.

In a possible implementation, the using the reference difference as the time domain sampling data of the current echo frame comprises: using, in response to the reference difference satisfying a reference difference threshold, the reference difference as the time domain sampling data of the current echo frame.

Figures 5, 6:
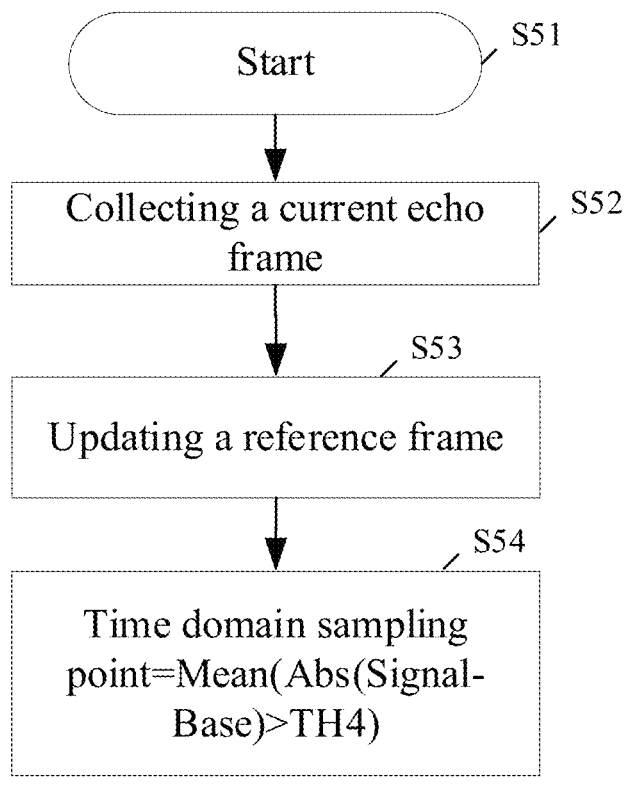
FIG. 5 is a flowchart of steps for converting a current echo frame received based on a target fly time into a time domain sampling signal according to an embodiment of the present disclosure.
FIG. 6 is a flowchart of steps for obtaining a heart rate value based on a time domain sampling signal according to an embodiment of the present disclosure.

It should be noted that in order to extract the heart rate in a time domain, each echo frame needs to be converted into a sampling data in the time domain. The specific conversion method is as shown in FIG. 5. The process starts (S51); collecting the current echo frame (S52); updating the reference frame (S53); calculating the difference between each pixel point corresponding to the current echo frame and the reference frame, extracting the absolute value of the difference since a phase change of the echo frame has a positive or negative value, then averaging absolute values of all differences, and using, in response to the average value being greater than the reference difference threshold TH4, the average value as the sampling data of the current echo frame in the time domain (S54).

In a possible implementation, as shown in FIG. 6, the step S240 includes: step S2401: filtering the time domain sampling signal to obtain a filtered time domain sampling signal; and step S2402: calculating the heart rate value based on the filtered time domain sampling signal.

Figure 7:
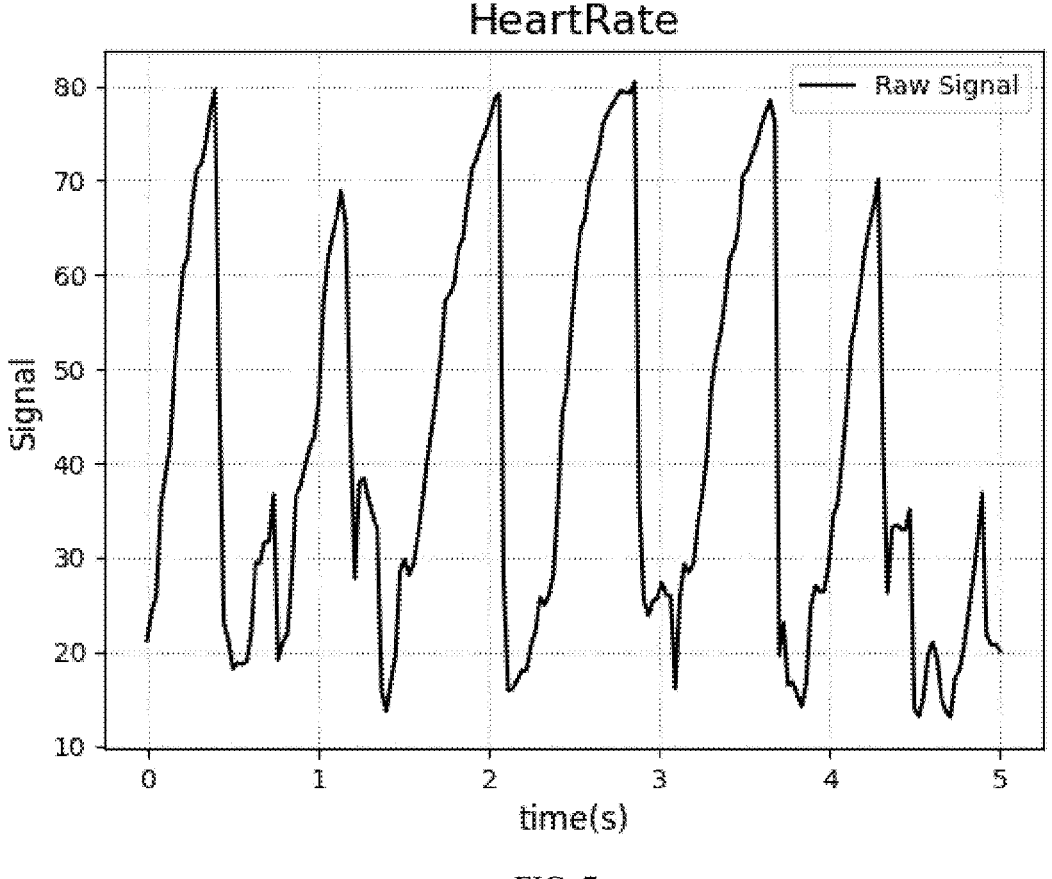
FIG. 7 is a schematic waveform diagram of a time domain sampling signal according to an embodiment of the present disclosure.

It should be noted that the time domain sampling signal may be used to calculate the heart rate in units of seconds, that is, calculate the heart rate once per second. The time domain sampling signal is as shown in FIG. 7.

Specifically, a heart rate calculation process is as shown in FIG. 8. The process starts (S81); calculating a smooth filtering curve for the time domain sampling signal (raw signal), wherein the filter window is a minimum heart rate cycle, and the smooth filtering curve is used as a DC component of the signal (S82); subtracting the smooth filtered DC curve from a raw signal curve to obtain an AC signal curve containing heart rate information (S83); performing Fourier transform and band-pass filtering on the AC curve, $f_{min} < f < f_{max}$, wherein $f_{min}$ and $f_{max}$ represent a minimum frequency (e.g., 0.6) and a maximum frequency (e.g., 4) of the heart rate respectively, and obtaining a filtered curve through inverse transform after filtering (S84); performing autocorrelation calculation on the filtered curve to obtain an autocorrelation curve (S85); determining a peak or valley of the autocorrelation curve (S86); and calculating the heart rate value (S87) following a heart rate calculation formula of $$HeartRate = \frac{f_{sample}}{N} \times 60,$$

wherein $f_{sample}$ is a sampling rate of an image of the ultrasonic chip, is a reciprocal of the fixed interval time T at which each frame of image is collected, $$f_{sample} = \frac{1}{T},$$

and N is an average interval of the peak or valley.

Preferably, autocorrelation calculation is performed on the filtered time domain sampling signal to obtain an autocorrelation signal; and the heart rate value is calculated based on the autocorrelation signal.

FIG. 9 is a schematic block diagram of an apparatus for ultrasonically measuring a heart rate via a finger according to another embodiment of the present disclosure. The solutions of the embodiments of the present disclosure can be applied to an electronic device, including but not limited to: a terminal device with a communication function, an electronic device with an interactive behavior capability, or the like.

The apparatus for ultrasonically measuring a heart rate via a finger in this embodiment comprises: a fly time determination module configured to acquire, when the finger presses a screen, a correspondence function between an echo signal and a fly time, and determine a target fly time based on the correspondence function, wherein the fly time is time elapsed from transmission to reception of an ultrasonic signal; an ultrasonic transceiver module configured to transmit the ultrasonic signal to the finger, and receive a current echo frame that is returned from the finger and carries fingerprint information of the finger based on the target fly time; a sampling signal processing module configured to determine a time domain sampling signal based on an inter-frame difference between the current echo frame and a reference frame; and a heart rate value calculation module configured to calculate a heart rate value based on the time domain sampling signal.

In some other examples, the fly time determination module is specifically configured to: determine a peak value of the correspondence function based on the correspondence function; and determine the target fly time based on the peak value of the correspondence function.

In some other examples, the sampling signal processing module is specifically configured to: calculate the inter-frame difference between the current echo frame and a last echo frame; and use a current echo frame satisfying an inter-frame difference threshold as the reference frame.

In some other examples, the sampling signal processing module is specifically configured to: calculate a continuous count value of current echo frames satisfying the inter-frame difference threshold; and use, in response to the continuous count value satisfying a count threshold, any one of the current echo frames corresponding to the continuous count value and satisfying the inter-frame difference threshold as the reference frame.

In some other examples, the sampling signal processing module is specifically configured to: calculate a reference difference between the current echo frame and the reference frame, use the reference difference as time domain sampling data of the current echo frame; and determine the time domain sampling signal based on the time domain sampling data.

In some other examples, the sampling signal processing module is specifically configured to: use, in response to the reference difference satisfying a reference difference threshold, the reference difference as the time domain sampling data of the current echo frame.

In some other examples, the heart rate value calculation module is specifically configured to: filter the time domain sampling signal to obtain a filtered time domain sampling signal; and calculate the heart rate value based on the filtered time domain sampling signal.

Figure 10:
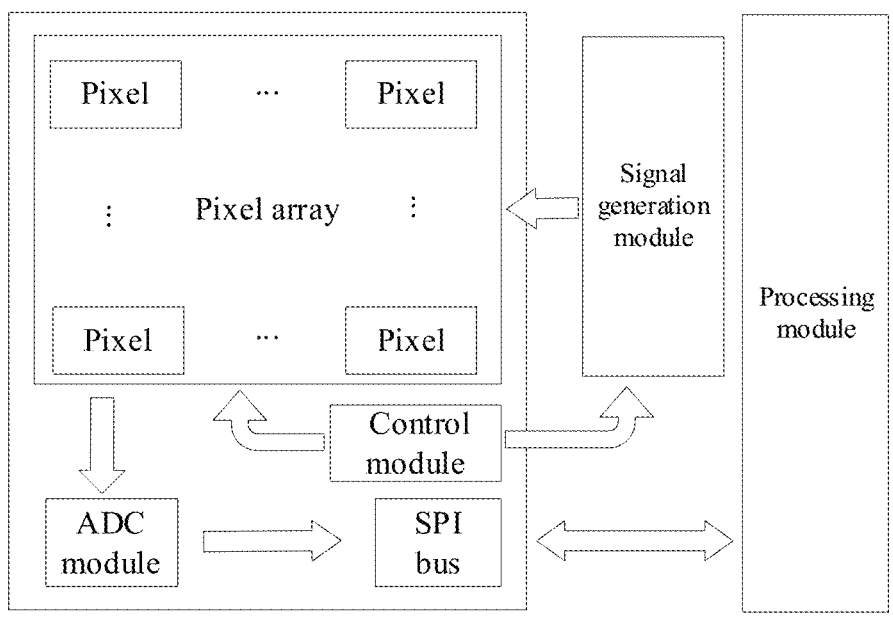
FIG. 10 is a schematic structural diagram of hardware framework of a system for ultrasonically measuring a heart rate via a finger according to an embodiment of the present disclosure.

Specifically, as shown in FIG. 10, the apparatus for ultrasonically measuring a heart rate via a finger may include: a pixel point array control transducer of M*N resolution, a control module, an ADC module, and a SPI bus. A signal generation module generates a drive voltage under the control of the control module to drive the transducer to emit an ultrasonic signal. After the ultrasonic signal is emitted and waiting until the end of the fly time, the control module controls the transducer to be switched to an acoustic wave receiving mode. The transducer converts a received acoustic wave signal into an electrical signal. The ADC converts the electrical signal into a digital signal and transmits it through the SPI to a processing module.

Figure 11:
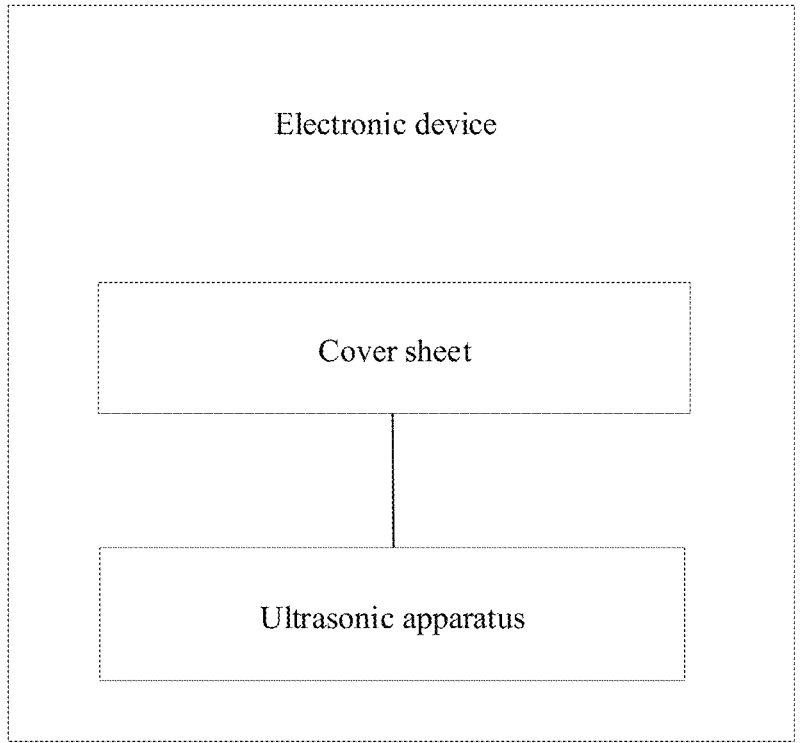
FIG. 11 is a schematic structural diagram of an electronic device according to an embodiment of the present disclosure.

As shown in FIG. 11, the ultrasonic fingerprint apparatus is arranged below a cover sheet of an electronic device to implement under-display ultrasonic fingerprint identification. The cover sheet may be made of a material, such as glass or plastic.

The above embodiments are only used to illustrate the embodiments of the present disclosure, and are not intended to limit the embodiments of the present disclosure. Those of ordinary skills in the relevant technical field may further make various alterations and modifications without departing from the spirit and scope of the embodiments of the present disclosure. Therefore, all equivalent technical solutions are also encompassed within the scope of the embodiments of the present disclosure, and the scope of patent protection of the embodiments of the present disclosure should be defined by the appended claims. The system, apparatus, modules, or units illustrated in the above embodiments may be specifically implemented by a computer chip or entity, or by a product having a function.

For ease of description, the above apparatus is described by dividing the apparatus into various units based on functions, and then describing the units respectively. Of course, when the present disclosure is implemented, the functions of the units may be implemented in a same piece or more pieces of software and/or hardware.

Those skilled in the art should understand that the embodiments of the present disclosure may be provided as a method, a system, or a computer program product. Accordingly, the present disclosure may take the form of an entirely hardware embodiment, an entirely software embodiment, or an embodiment combining software and hardware. Further, the present disclosure may take the form of a computer program product embodied on one or more computer-usable storage mediums (including, but not limited to, a disk memory, a CD-ROM, an optical memory, and the like) having a computer-usable program code embodied thereon.

The present disclosure is described with reference to the flow charts and/or block diagrams of the method, device (system), and computer program product according to the embodiments of the present disclosure. It should be understood that each process and/or block in the flow charts and/or block diagrams as well as combinations of processes and/or blocks in the flow charts and/or block diagrams may be implemented by computer program instructions. The computer program instructions may be provided to a processor of a general purpose computer, a special purpose computer, an embedded processing machine, or other programmable data processing devices to produce a machine, thereby producing an apparatus for implementing the functions specified in one or more processes in the flow charts and/or one or more blocks in the block diagrams based on the instructions executed by the processor of the computer or other programmable data processing devices.

These computer program instructions may also be stored in a computer-readable memory that can direct a computer or other programmable data processing devices to function in a particular manner, such that the instructions stored in the computer-readable memory produce an article of manufacture including an instruction apparatus which implements the functions specified in one or more processes in the flow charts and/or one or more blocks in the block diagrams.

The computer program instructions may also be loaded onto a computer or other programmable data processing devices, to cause a series of operational steps to be executed on the computer or other programmable devices, to produce a computer implemented process, such that the instructions executed on the computer or other programmable devices provide steps for implementing the functions specified in one or more processes in the flow charts and/or one or more blocks in the block diagrams.

In a typical configuration, a computing device includes one or more processors (CPU), an input/output interface, a network interface, and an internal memory. The internal memory may include forms, such as a volatile memory, a random-access memory (RAM), and/or a nonvolatile internal memory, e.g., a read-only memory (ROM) or a flash RAM, in a computer-readable medium. The internal memory is an example of the computer-readable medium.

The computer-readable medium includes permanent and non-permanent mediums, removable and non-removable mediums, and information storage may be implemented by any method or technology. The information may be a computer-readable instruction, a data structure, a program module, or other data. Examples of computer storage mediums include, but are not limited to, a phase-change random-access memory (PRAM), a static random-access memory (SRAM), a dynamic random-access memory (DRAM), a random-access memory (RAM) of other type, a read-only memory (ROM), an electrically erasable programmable read-only memory (EEPROM), a flash RAM or other internal memory technology, a compact disc read-only memory (CD-ROM), a digital versatile disc (DVD) or other optical storage, a magnetic cassette tape, a magnetic tape or disk storage or other magnetic storage devices, or any other non-transmission medium, which may be configured to store information accessible to a computing device. As defined herein, the computer-readable medium excludes transitory media, e.g., a modulated data signal or carrier wave.

It should be further noted that the terms such as "comprising," "including," or any other variation thereof are intended to encompass non-exclusive inclusions, such that a process, a method, an article, or a device that includes a series of elements not only includes those elements, but also includes other elements that are not explicitly listed, or further includes elements that are inherent to such a process, method, article, or device. In the case of no more constraints, an element defined by the wording "comprise a . . . " does not preclude the existence of additional identical elements in a process, a method, an article, or a device that includes the element.

Those skilled in the art should understand that the embodiments of the present disclosure may be provided as a method, a system, or a computer program product. Accordingly, the present disclosure may take the form of an entirely hardware embodiment, an entirely software embodiment, or an embodiment combining software and hardware. Further, the present disclosure may take the form of a computer program product embodied on one or more computer-usable storage mediums (including, but not limited to, a disk memory, a CD-ROM, an optical memory, and the like) having a computer-usable program code embodied thereon.

The present disclosure may be described in a general context of computer-executable instructions executed by a computer, e.g., program modules. Generally, the program modules include routines, programs, objects, components, data structures, etc. that execute particular tasks or implement particular abstract data types. The present disclosure may also be practiced in distributed computing environments. In these distributed computing environments, tasks are executed by remote processing devices connected through a communication network. In a distributed computing environment, the program modules may be located in local and remote computer storage mediums including storage devices.

The embodiments in the present specification are described progressively, identical or similar portions between the embodiments may be mutually referred to, and differences of each embodiment from other embodiments are mainly described in the embodiment. In particular, system embodiments are substantially similar to method embodiments, and therefore are relatively simply described. A part of description of the method embodiments may be referred to for relevant details.

The invention claimed is:

1. A method for ultrasonically measuring a heart rate via a finger, being applied to an ultrasonic fingerprint apparatus, the ultrasonic fingerprint apparatus being arranged below a cover sheet of an electronic device to implement under-display ultrasonic fingerprint identification, the method comprising:

acquiring, when the finger presses a screen, a correspondence function between an echo signal and a fly time, and determining a target fly time based on the correspondence function, wherein the fly time is a time elapsed from transmission to reception of an ultrasonic signal;

transmitting the ultrasonic signal to the finger, and receiving a current echo frame that is returned from the finger and carries fingerprint information of the finger based on the target fly time;

determining a time domain sampling signal based on an inter-frame difference between the current echo frame and a reference frame; and calculating a heart rate value based on the time domain sampling signal;

wherein the method further comprises:

calculating a difference between pixel points of the current echo frame and corresponding pixel points of a last echo frame as an inter-frame difference between the current echo frame and the last echo frame; and using, in response to the inter-frame difference between the current echo frame and the last echo frame satisfying an inter-frame difference threshold, the current echo frame as the reference frame.

2. The method according to claim 1, wherein the determining the target fly time based on the correspondence function comprises:

determining a peak value of the correspondence function based on the correspondence function; and determining the target fly time based on the peak value of the correspondence function, wherein the target fly time is a fly time corresponding to the obtaining of a maximum echo signal.

3. The method according to claim 1, wherein the using, in response to the inter-frame difference between the current echo frame and the last echo frame satisfying the inter-frame difference threshold, the current echo frame as the reference frame comprises:

maintaining a continuous count value of current echo frames that satisfy the inter-frame difference threshold;

comparing the continuous count value with a count threshold; and updating the reference frame by using, based on the comparison showing that the continuous count value satisfies a count threshold, any one of the current echo frames that satisfy the inter-frame difference threshold and correspond to the continuous count value as the reference frame.

4. The method according to claim 3, wherein the determining the time domain sampling signal based on the inter-frame difference between the current echo frame and the reference frame comprises:

calculating a reference difference between the current echo frame and the reference frame, and using the reference difference as time domain sampling data of the current echo frame; and determining the time domain sampling signal based on the time domain sampling data.

5. The method according to claim 4, wherein the using the reference difference as the time domain sampling data of the current echo frame comprises:

comparing the reference difference with a reference difference threshold; and determining, based on the comparison showing that the reference difference satisfies a reference difference threshold, the reference difference as the time domain sampling data of the current echo frame.

6. The method according to claim 5, wherein the calculating the heart rate value based on the time domain sampling signal comprises:

filtering the time domain sampling signal to obtain a filtered time domain sampling signal; and calculating the heart rate value based on the filtered time domain sampling signal.

7. An electronic device, comprising: a processor, a memory, a communication interface, and a communication bus, wherein the processor, the memory, and the communication interface are configured to communicate with each other through the communication bus; the memory is configured to store at least one executable instruction, and the executable instruction causes the processor to execute a method for ultrasonically measuring a heart rate via a finger, being applied to an ultrasonic fingerprint apparatus, the ultrasonic fingerprint apparatus being arranged below a cover sheet of the electronic device to implement under-display ultrasonic fingerprint identification, the method comprising:

acquiring, when the finger presses a screen, a correspondence function between an echo signal and a fly time, and determining a target fly time based on the correspondence function, wherein the fly time is a time elapsed from transmission to reception of an ultrasonic signal;

transmitting the ultrasonic signal to the finger, and receiving a current echo frame that is returned from the finger and carries fingerprint information of the finger based on the target fly time;

determining a time domain sampling signal based on an inter-frame difference between the current echo frame and a reference frame; and calculating a heart rate value based on the time domain sampling signal;

wherein the method further comprises:

calculating a difference between pixel points of the current echo frame and corresponding pixel points of a last echo frame as an inter-frame difference between the current echo frame and the last echo frame; and using, in response to the inter-frame difference between the current echo frame and the last echo frame satisfying an inter-frame difference threshold, the current echo frame as the reference frame.

8. The electronic device according to claim 7, wherein the determining the target fly time based on the correspondence function comprises:

determining a peak value of the correspondence function based on the correspondence function; and determining the target fly time based on the peak value of the correspondence function, wherein the target fly time is a fly time corresponding to the obtaining of a maximum echo signal.

9. The electronic device according to claim 7, wherein the using, in response to the inter-frame difference between the current echo frame and the last echo frame satisfying the inter-frame difference threshold, the current echo frame as the reference frame comprises:

maintaining a continuous count value of current echo frames that satisfy the inter-frame difference threshold;

comparing the continuous count value with a count threshold; and updating the reference frame by using, based on the comparison showing that the continuous count value satisfies a count threshold, any one of the current echo frames that satisfy the inter-frame difference threshold and correspond to the continuous count value as the reference frame.

10. The electronic device according to claim 9, wherein the determining the time domain sampling signal based on the inter-frame difference between the current echo frame and the reference frame comprises:

calculating a reference difference between the current echo frame and the reference frame, and using the reference difference as time domain sampling data of the current echo frame; and determining the time domain sampling signal based on the time domain sampling data.

11. The electronic device according to claim 10, wherein the using the reference difference as the time domain sampling data of the current echo frame comprises:

comparing the reference difference with a reference difference threshold; and determining, based on the comparison showing that the reference difference satisfies a reference difference threshold, the reference difference as the time domain sampling data of the current echo frame.

12. The electronic device according to claim 11, wherein the calculating the heart rate value based on the time domain sampling signal comprises:

filtering the time domain sampling signal to obtain a filtered time domain sampling signal; and calculating the heart rate value based on the filtered time domain sampling signal.

* * * * *